(12) United States Patent
Thépot et al.

(10) Patent No.: US 6,447,708 B1
(45) Date of Patent: Sep. 10, 2002

(54) SULPHUR PRODUCTS FOR ADDING A POLYTHIOL ON A NORBORNENE DERIVATIVE, PREPARATION METHOD AND USE FOR OBTAINING RADICAL CROSS-LINKING PRODUCTS

(75) Inventors: Philippe Thépot, Liancourt (FR); Henri Strub, Pont St. Maxence (FR)

(73) Assignee: Cray Valley S.A., Verneuil en Halatte (FR)

( * ) Notice: Subject to any disclaimer, the term of this patent is extended or adjusted under 35 U.S.C. 154(b) by 0 days.

(21) Appl. No.: 09/647,669

(22) PCT Filed: Apr. 1, 1999

(86) PCT No.: PCT/FR99/00766

§ 371 (c)(1),
(2), (4) Date: Sep. 29, 2000

(87) PCT Pub. No.: WO99/51663

PCT Pub. Date: Oct. 14, 1999

(30) Foreign Application Priority Data

Apr. 3, 1998 (FR) .............................. 98 04166

(51) Int. Cl.⁷ .......................... C08G 75/04; C08F 2/50; B29C 35/08
(52) U.S. Cl. ...................... 264/496; 522/146; 522/162; 522/180; 526/286; 526/289; 528/376
(58) Field of Search ................................ 522/180, 162, 522/146; 528/376; 526/286, 289; 264/496

(56) References Cited

U.S. PATENT DOCUMENTS

| | | | |
|---|---|---|---|
| 3,734,968 A | | 5/1973 | Hickner et al. |
| 3,839,464 A | | 10/1974 | Najer et al. |
| 4,808,638 A | * | 2/1989 | Steinkraus et al. ......... 522/167 |
| 5,167,882 A | * | 12/1992 | Jacobine et al. ......... 156/273.3 |
| 5,266,670 A | * | 11/1993 | Nakos et al. ................ 528/32 |
| 5,371,181 A | * | 12/1994 | Glaser et al. ............... 522/180 |
| 5,459,175 A | * | 10/1995 | Woods et al. ............... 522/180 |

FOREIGN PATENT DOCUMENTS

JP        2294322     12/1990

OTHER PUBLICATIONS

Chemical Abstracts Accession No. 114:248656 XP002090932 for JP 02 294322A Showa High Polymer Co. Ltd.

* cited by examiner

*Primary Examiner*—Susan W. Berman
(74) *Attorney, Agent, or Firm*—Michael B. Fein; Cozen O'Connor

(57) ABSTRACT

Sulphur product, (P), process for making (P), films, molded articles made therefrom, wherein (P) is obtained by the addition reaction of at least one polythiol (I) with at least one compound of formula (II):

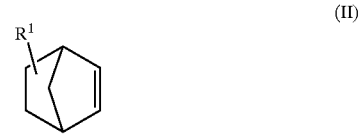

(II)

in which $R^1$ represents a linear or branched aliphatic residue comprising an ethylenic unsaturation double bond, it being optional for the latter to be that by which $R^1$ is connected to the norbornene ring, it also being optional for the said ring to comprise other substituents chosen from $C_1$–$C_3$ alkyl groups, in proportions corresponding or substantially corresponding to one thiol group of the polythiol or polythiols (I) per mole of the compound or compounds (II), the thiol groups of the compound or compounds (I) adding predominantly to the cyclic double bond of the compound or compounds (II) and, on average, one ethylenic unsaturation of a compound (II) of the two which it carries remaining free; or sulphur product, (P'), obtained by the addition reaction of at least one polythiol (I) with at least one sulphur product (P), the double bonds of the said sulphur product (P) having been completely or substantially completely consumed, the sulphur product (P') obtained being a crosslinked product.

19 Claims, No Drawings

SULPHUR PRODUCTS FOR ADDING A POLYTHIOL ON A NORBORNENE DERIVATIVE, PREPARATION METHOD AND USE FOR OBTAINING RADICAL CROSS-LINKING PRODUCTS

The present invention relates to novel sulphur products from the addition of at least one polythiol to at least one norbornene derivative comprising an exocyclic ethylenic unsaturation, to a process of manufacture of these sulphur products, to a composition which can be crosslinked by the radical route comprising such a sulphur product in the crosslinkable state, and to the resulting crosslinked products and their manufacture.

The invention is targeted at broadening the range of these sulphur products which are of advantage in various fields: optical materials, coatings and adhesives, and for which the mechanical properties can be varied as a function of the polythiol.

In particular, it is desired to produce, for optical applications, products which can be crosslinked by the radical route, in particular by the photochemical route, to give crosslinked materials with a high refractive index, by more specifically targeting, in this case, products having the highest possible sulphur content in order to further improve the refractive index of these materials.

Reaction products of polythiols and of unsaturated alicylic compounds having at least two unsaturations per molecule, at least one of them being a cyclic unsaturation, have been generally disclosed.

However, experiments carried out by the Applicant Company have allowed it to be found that:
  the direct crosslinking of a mixture of polythiol and of vinylnorbornene is not always possible: the mixture of tri- or tetrathiols tested with vinylnorbornene was a two-phase mixture; the dithiols tested gave a homogeneous mixture with vinylnorbornene but the addition of a photoinitiator did not make possible crosslinking under UV;
  the reaction by the thermal route of a polythiol and of dicyclopentadiene with one thiol group per mole of dicyclopentadiene results in a product which does not crosslink under UV with a polythiol as crosslinking agent.

It is under these circumstances that the Applicant Company has discovered that, surprisingly, a specific family of compounds, namely substituted norbornenes comprising an exocyclic unsaturation, gives with polythiols, under stoichiometric conditions of one or of approximately one thiol group per one mole of the norbornene in question, addition products which can subsequently be crosslinked under UV and generally by the radical route in the presence of at least one polythiol.

It is thus possible to prepare materials with a high sulphur content, corresponding to the targeted objectives, by first preparing a liquid crosslinkable sulphur product (P) which will constitute the starting material for the formulation of a product (P) or of a composition which can be crosslinked in the desired form: film or moulded item. The said sulphur product (P) does not exhibit the disadvantages of the polythiols and of the norbornene derivatives from which it is obtained, which products are volatile, have an unpleasant smell and are toxic. The formulator of the product (P') or of the crosslinkable composition will then handle products which are nontoxic and odourless or with a very slight smell.

A first subject-matter of the present invention is therefore a sulphur product obtained by the addition reaction of at least one polythiol (I)

(A) with at least one compound of formula (II):

in which $R^1$ represents a linear or branched aliphatic residue comprising an ethylenic unsaturation double bond, it being possible for the latter to be that by which $R^1$ is connected to the norbornene ring, it also being possible for the said ring to comprise other substituents chosen from $C_1$–$C_3$ alkyl groups, in proportions corresponding or substantially corresponding to one thiol group of the polythiol or polythiols (I) per mole of the compound or compounds (II), the thiol groups of the compound or compounds (I) adding predominantly to the cyclic double bond of the compound or compounds (II) and, on average, one ethylenic unsaturation of a compound (II) of the two which it carries remaining free; or (B) with at least one crosslinkable product (P), such as obtained in accordance with point (A) above, the double bonds of the said product (P) having been completely or substantially completely consumed, the product (P') obtained being a crosslinked product.

The polythiol or polythiols (I) which have been used to form the crosslinked product (P') are not necessarily the same as those which have been used to form the crosslinkable product (P).

The crosslinked product (P') is obtained with a polythiol (I) with an SH functionality of at least 2 in the case where the crosslinkable product (P) has a functionality of ethylenic unsaturations of at least 3 and with a polythiol (I) with an SH functionality of at least 3 in the case where the crosslinkable product (P) has a functionality of ethylenic unsaturations of at least 2. In the case where mixtures of polythiols are used for the crosslinking, their mean SH functionality will be at least 2.

The compound of formula (II) is in particular 5-vinyl-2-norbornene (5-vinylbicyclo[2.2.1]hept-2-ene) or 5-ethylidene-2-norbornene (5-ethylidenebicyclo[2.2.1]hept-2-ene).

The polythiols (I) are chosen in particular from the compounds of formula $R^2$—[—SH]$_n$, in which:
  $R^2$ is an n-valent aliphatic, aromatic or heterocyclic radical or an n-valent radical comprising a combination of these, it being possible for $R^2$ to comprise substituents, it being possible for the backbone or the substituents to be interrupted by at least one heteroatom chosen from —O— or —S— and/or one group chosen from

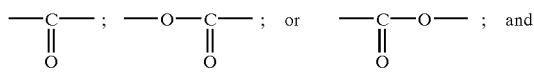

n is an integer from 2 to 6.

The polythiols (I) can be polythiols obtained by addition of a polythiol of formula $R^2$—[—SH]$_n$, in which $R^2$ and n are as defined above, to a compound of formula (II) as defined above, with an excess of thiol and under addition conditions which prevent crosslinking, on the basis of the Makosco-Miller relationship (Macromolecules, 1976, volume 9, pages 199–211).

Examples of polythiols comprise:
(1) aliphatic polythiols, such as methanedithiol, 1,2-ethanedithiol, 1,1-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutene-1,2-dithiol, bicyclo[2.2.1]-heptane-exo-cis-2,3-dithiol, 1,1-bis(mercaptomethyl)cyclohexane, thiomalic acid bis(2-mercaptoethyl ester), 2,3-dimercaptosuccinic acid 2-mercaptoethyl ester, 2,3-dimercapto-1-propanol 2-mercaptoacetate, 2,3-dimercapto-1-propanol 3-mercaptopropionate, diethylene glycol bis(2-mercaptoacetate), diethylene glycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethylene glycol bis(2-mercaptoacetate), ethylene glycol bis(3-mercaptopropionate), trimethylolpropane tris(3-mercaptopropionate), trimethylolpropane tris(2-mercaptoacetate), pentaerythritol tetrakis(3-mercaptopropionate), pentaerythritol tetrakis(2-mercaptoacetate), polyethylene glycol dimercaptoacetates and polyethylene glycol di(mercaptopropionates), and these same compounds substituted by halogen, such as chlorine and bromine;
(2) aromatic polythiols, such as 1,2-dimercaptobenzene, 4-t-butyl-1,2-benzenedithiol, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2-bis(mercaptomethyleneoxy)benzene, 1,3-bis(mercaptomethyleneoxy)benzene, 1,4-bis(mercaptomethyleneoxy)benzene, 1,2-bis(mercaptoethyleneoxy)benzene, 1,3-bis(mercaptoethyleneoxy)benzene, 1,4-bis(mercaptoethyleneoxy)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 1,2,3-tris(mercaptomethyleneoxy)benzene, 1,2,4-tris(mercaptomethyleneoxy)benzene, 1,3,5-tris(mercaptomethyleneoxy)benzene, 1,2,3-tris(mercaptoethyleneoxy)benzene, 1,2,4-tris(mercaptoethyleneoxy)benzene, 1,3,5-tris(mercaptoethyleneoxy)benzene, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethylbenzene), 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 1,2,3,4-tetrakis(mercaptomethyleneoxy)benzene, 1,2,3,5-tetrakis(mercaptomethyleneoxy)benzene, 1,2,4,5-tetrakis(mercaptomethyleneoxy)benzene, 1,2,3,4-tetrakis(mercaptoethyleneoxy)benzene, 1,2,3,5-tetrakis(mercaptoethyleneoxy)benzene, 1,2,4,5-tetrakis(mercaptoethyleneoxy)benzene, 2,2'-dimercaptobiphenyl, 4,4'-dimercaptobiphenyl, 4,4'-dimercaptodibenzyl, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 9,10-anthracenedimethanethiol, 1,3-di(p-methoxyphenyl)propane-2,2-dithiol, 1,3-diphenylpropane-2,2-dithiol, phenylmethane-1,1-dithiol and 2,4-di(p-mercaptophenyl)pentane;
(3) halogenated aromatic polythiols comprising chlorinated and brominated aromatic polythiols, such as 2,5-dichlorobenzene-1,3-dithiol, 1,3-di(p-chlorophenyl)propane-2,2-dithiol, 3,4,5-tribromo-1,2-dimercaptobenzene and 2,3,4,6-tetrachloro-1,5-bis(mercaptomethyl)benzene;
(4) heterocyclic polythiols, such as 2-methylamino-4,6-dimercapto-sym-triazine, 2-ethylamino-4,6-dimercapto-sym-triazine, 2-amino-4,6-dimercapto-sym-triazine, 2-morpholino-4,6-dimercapto-sym-triazine, 2-cyclohexylamino-4,6-dimercapto-sym-triazine, 2-methoxy-4,6-dimercapto-sym-triazine, 2-phenoxy-4,6-dimercapto-sym-triazine, 2-thiobenzeneoxy-4,6-dimercapto-sym-triazine, 2-thiobutyloxy-4,6-dimercapto-sym-triazine and 2-thiobutyloxy-4,6-dimercapto-sym-triazine, and these same compounds substituted by halogen, such as chlorine and bromine;
(5) polythiols having at least one sulphur atom in addition to the mercapto groups and comprising:
   (5a) aromatic polythiols, such as 1,2-bis(mercaptomethylthio)benzene, 1,3-bis(mercaptomethylthio)benzene, 1,4-bis(mercaptomethylthio)benzene, 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene, 1,3,5-tris(mercaptoethylthio)benzene, 1,2,3,4-tetrakis(mercaptomethylthio)benzene, 1,2,3,5-tetrakis(mercaptomethylthio)benzene, 1,2,4,5-tetrakis(mercaptomethylthio)benzene, 1,2,3,4-tetrakis(mercaptoethylthio)benzene, 1,2,3,5-tetrakis(mercaptoethylthio)benzene, 1,2,4,5-tetrakis(mercaptoethylthio)benzene, and the derivatives alkylated on the aromatic ring of these polythiols; and 4,4'-thiodibenzenethiol;
   (5b) aliphatic polythiols, such as bis(mercaptomethyl) sulphide, bis(2-mercaptoethyl) sulphide, bis(2-mercaptopropyl) sulphide, bis(mercaptomethylthio)methane, bis(2-mercaptoethylthio)methane, bis(3-mercaptopropylthio)methane, tetrakis(7-mercapto-2,5-dithiaheptyl)methane, 1,2-bis(mercaptomethylthio)ethane, 1,2-bis(2-mercaptoethylthio)ethane, 1,2-bis(3-mercaptopropylthio)ethane, 1,3-bis(mercaptomethylthio)propane, 1,2-bis(2-mercaptoethylthio)propane, 1,2-bis(3-mercaptopropylthio)propane, 1,2,3-tris(mercaptomethylthio)propane, 1,2,3-tris(2-mercaptoethylthio)propane, 1,2,3-tris(3-mercaptopropylthio)propane, tetrakis(mercaptomethylthiomethyl)methane, tetrakis(2-mercaptoethylthiomethyl)methane, tetrakis(3-mercaptopropylthiomethyl)methane, bis(2,3-dimercaptopropyl) sulphide, 2,5-dimercapto-1,4-dithiane, bis(mercaptomethyl) disulphide, bis(mercaptoethyl) disulphide and bis(mercaptopropyl) disulphide, the esters of thioglycolic acid and of mercaptopropionic acid with these compounds, hydroxymethyl sulphide bis(2-mercaptoacetate), hydroxymethyl sulphide bis(3-mercaptopropionate), hydroxyethyl sulphide bis(2-mercaptoacetate), hydroxyethyl sulphide bis(3-mercaptopropionate), hydroxypropyl sulphide bis(2-mercaptoacetate), hydroxypropyl sulphide bis(3-mercaptopropionate), hydroxymethyl disulphide bis(2-mercaptoacetate), hydroxymethyl disulphide bis(3-mercaptopropionate), hydroxyethyl disulphide bis(2-mercaptoacetate), hydroxyethyl disulphide bis(3-mercaptopropionate), hydroxypropyl disulphide bis(2-mercaptoacetate), hydroxypropyl disulphide bis(3-mercaptopropionate), 2-mercaptoethyl ether bis(2-mercaptoacetate), 2-mercaptoethyl ether bis(3-mercaptopropionate), 1,4-dithiane-2,5-diol bis(3-mercaptopropionate), thioglycolic acid bis(2-mercaptoethyl ester), thiodipropionic acid bis(2-mercaptoethyl ester), 4,4'-thiodibutyric acid bis(2-mercaptoethyl ester), dithiodiglycolic acid bis(2-mercaptoethyl ester), dithiodipropionic acid bis(2-mercaptoethyl ester), 4,4'-dithiodibutyric acid bis(2-mercaptoethyl ester), thiodiglycolic acid bis(2,3-dimercaptopropyl ester), thiodipropionic acid bis(2,3-dimercaptopropyl ester), dithiodiglycolic acid bis(2,3-dimercaptopropyl ester) and dithiodiproprionic acid bis(2,3-dimercaptopropyl ester), and these same compounds substituted by halogen, such as chlorine and bromine; 4-mercaptomethyl-3,6-dithia-1,8-octanedithiol; and (5c) heterocyclic compounds, such as 3,4-thiophenedithiol, 2,5-bis(mercaptomethyl) tetrahydrothiophene, bis(mercaptomethyl)-1,3-dithiolane, 2,5-dimercapto-1,3,4-diazole, 2,5-dimercapto-1,4-dithiane and 2,5-dimercaptomethyl-1, 4-dithiane, and these same compounds substituted by halogen, such as chlorine or bromine; and tris(3-mercaptopropyl) isocyanurate; and (6) reaction products of polythiols with polyunsaturated compounds (excess of SH/unsaturations), such as 5-ethylidene-2-norbornene or dicyclopentadiene-pentaerythritol tetrakis(mercaptoacetate) addition products.

Another subject-matter of the present invention is a process for the manufacture of a sulphur product as defined above, characterized in that a mixture of at least one polythiol (I) as defined above and of at least one compound (II) as defined above is reacted at a temperature from 30 to 170° C., the proportions of the compounds (I) and (II) being chosen so that there is or that there is substantially one thiol group of the compound or compounds (I) per one mole of the compound or compounds (II), in order to obtain the crosslinkable product (P), and that, in order to obtain the product (P'), a mixture of the product (P) thus obtained and of at least one compound of formula (I) is reacted by the radical route in stoichiometric proportions or substantially stoichiometric proportions between the thiol groups and the double bonds, it being possible for the radicals to be generated thermally and/or by way of UV or visible irradiation or by way of an electron beam.

The reaction of the compounds (I) and (II) can be carried out in the presence of at least one catalyst chosen in particular from free radical initiators, such as peroxides, for example benzoyl peroxide, p-chlorobenzoyl peroxide and other diacyl peroxides, or di-tert-butyl peroxide; peroxy esters, such as t-butyl peroxy-2-ethylhexanoate or t-butyl peroxyneodecanoate; peroxydicarbonates, such as diisopropyl peroxydicarbonate or di(2-ethylhexyl) peroxydicarbonate; and azo compounds, such as azobisisobutyronitrile; and from Lewis acids, such as hydrogen tetrafluoroborate, boron trifluoride and the coordination complexes of the latter with water, esters, aldehydes, alcohols, acids, ketones or ethers, such as $BF_3.(H_2O)_x$ (x=1 or 2), $BF_3.C_4H_9OH$, $BF_3.2CH_3COOH$, $BF_3.2CH_3COOC_2H_5$, $BF_3.CH_3.COCH_3$, $BF_3.O(C_2H_5)_2$ or $BF_3.C_4H_9OC_4H_9$; hydrochloric acid, sulphuric acid, sulphuric acid esters, such as ethyl sulphuric acid, organic sulphonic acids, such as toluenesulphonic acid or butanesulphonic acid; and amines, such as triethylamine. The catalyst can be used, per one thiol functional group of the polythiol (I), for example in the proportion of 0.0001 to 0.5 mol in the case of peroxides, peroxy esters, peroxycarbonates and azo compounds, of 0.01 to 2.0 mol in the case of acids and Lewis acids, or of 0.05 to 0.1 mol in the case of amines.

The reaction of the compounds (I) and (II) can be carried out in the absence of solvent or in the presence of a solvent, which can in particular be an aromatic, aliphatic or cycloaliphatic solvent, the said solvent being removed at the end of the reaction.

The reaction of the polythiol or polythiols (I) with the product (P) can be carried out photochemically, in which case the reaction can be carried out in the absence of a photoinitiator or photoinitiating system, or in the presence of at least one photoinitiator or of a photoinitiating system, which can be used in combination with a photoactivating agent. It is also possible to carry out the reaction by way of UV irradiation, without photoinitiator.

The photoinitiator used according to the invention can be any compound capable of generating free radicals under the effect of ultraviolet radiation.

Mention may be made, by way of examples, of:

α-diketones, such as benzil and diacetyl;

acyloins, such as benzoin;

acyloin ethers, such as benzoin methyl ether, benzoin ethyl ether, benzoin isopropyl ether and benzoin isobutyl ether;

thioxanthones, such as thioxanthone, 2,4-diethylthioxanthone, thioxanthone-1-sulphonic acid, isopropyl thioxanthone-4-sulphonate, isopropylthioxanthone and 2-chlorothioxanthone;

benzophenones, such as benzophenone, 4,4'-bis (dimethylamino)benzophenone, 4,4'-bis(diethylamino) benzophenone, 4,4'-diethylaminobenzophenone or Mischler's ketone;

propiophenones, such as 2-hydroxy-2-methylpropiophenone or 4'-isopropyl-2-hydroxy-2-methylpropiophenone;

acetophenones, such as acetophenone, p-dimethylaminoacetophenone, α,α'-dimethoxyacetoxyacetophenone, 2,2-dimethoxy-2-phenylacetophenone, p-methoxyacetophenone, 2-methyl-1-[4-(methylthio)phenyl]-2-morpholino-1-propanone, 2,2-diethoxyacetophenone, 4'-phenoxy-2,2-dichloroacetophenone, 2-benzyl-2-(N,N-dimethylamino)-1-(4-morpholinophenyl)-1-butanone, 2,2-dimethoxy-2-phenylacetophenone or 2-hydroxy-2-methyl-1-phenylpropanone;

quinones, such as anthraquinone, 2-ethylanthraquinone, 2-chloroanthraquinone or 1,4-naphthoquinone;

α-hydroxy aryl ketones, such as 1-hydroxycyclohexyl phenyl ketone;

halogenated compounds, such as phenacyl chloride, tribromomethyl phenyl sulphone or tris(trichloromethyl)-s-triazine;

monoacyl phosphine oxides, such as 2,4,6-trimethylbenzoyldiphenylphosphine oxide and 2,4,6-trimethylbenzoylethoxyphenylphosphine oxide;

bisacyl phosphine oxides, such as bis(2,6-dichlorobenzoyl) (4-propylphenyl)phosphine oxide, bis(2,6-dimethoxybenzoyl)(2,4,4-trimethylpentyl)phosphine oxide, bis(2,4,6-trimethylbenzoyl)phenylphosphine oxide and bis(2,4,6-trimethylbenzoyl) (2,4,4-trimethylpentyl) phosphine oxide;

α-sulphoketones; and other compounds, such as benzil dimethyl ketal, isoamyl N,N-dimethylaminobenzoate, ethyl N,N-dimethylaminobenzoate, benzoin benzoate, 2-hydroxy-2-methyl-1-phenylpropanone or α-acyloxime ester.

When a photoinitiator is used, the above compounds can be used either individually as photoinitiator or in the form of a mixture of at least two of them as photoinitiating system. Furthermore, at least one photoactivating agent can be used in combination with the initiator or with the photoinitiating system.

The proportion of photoinitiator or of photoinitiating system according to the invention is, for example, between 0.5 and 10% by weight approximately, preferably between 1 and 5% by weight approximately, with respect to the mass of the formulation of the product or products (P) with the polythiol or polythiols.

The reaction of the polythiol or polythiols (I) with the product (P) can also be carried out thermally, in which case the reaction is advantageously carried out in the presence of at least one initiator, a producer of free radicals, which can be used in combination with an accelerator.

The initiator is composed in particular of at least one from an organic peroxide, such as benzoyl peroxide, 2,5-dimethyl-2,5-bis(2-ethylhexylperoxy)hexane, methyl ethyl ketone peroxide or 2,4-pentanedione peroxide; a peroxydicarbonate; or a peroxy ester, such as tert-butyl peroxybenzoate, tert-butyl peroxyoctoate, tert-amyl peroxyoctoate or 2,5-diperoxyoctoate. This initiator is used in particular in a proportion of 0.5 to 3% by weight with respect to the mass of the formulation of the product or products (P) with the polythiol or polythiols.

Mention may in particular be made, as thermal crosslinking accelerator preferably used in a proportion of 0.1 to 1% by weight with respect to the mass of the formulation of the product or products (P) with the polythiol or polythiols, of solutions, in an organic solvent, of dioctyl phthalate, of inorganic or organic salts of transition metals, such as vanadium, chromium, manganese, iron, cobalt, nickel, copper, zinc, molybdenum and lead, or of tertiary amines, such as dimethylaniline or N,N-dimethyl-para-toluidine.

When the intitiating peroxide is benzoyl peroxide, it is preferable to use a tertiary amine as accelerator. When the initiating peroxide is methyl ethyl ketone peroxide, it is preferable to use a salt such as cobalt naphthenate or octoate as accelerator.

It is also possible to simultaneously use a photoinitiator or photoinitiating system and, if appropriate, a photoactivating agent, and a thermal crosslinking initiator with, if appropriate, an accelerator.

The reaction mixture of the polythiol or polythiols (I) and of the reaction product (P) can be deposited as a thin layer on a substrate and the reaction can be carried out by the radical route in order to obtain the crosslinked product (P') in the form of a film; it is also possible to introduce the reaction mixture of the polythiol or polythiols (I) and of the reaction product (P) into a mould and to carry out the reaction by the radical route in order to obtain the crosslinked product (P') in the form of a moulded item, the mould being a mould which is transparent to at least a portion of the radiation with wavelengths of between 180 and 400 nm in the case where the photochemical route is used.

The present invention also relates to a composition which can be crosslinked by the radical route, it being possible for the radicals to be generated thermally and/or by way of UV or visible irradiation or by way of an electron beam, characterized in that it comprises at least one crosslinkable product (P) as defined above.

In particular, the said composition comprises:

(a) at least one crosslinkable product (P) as defined above;

(b) at least one crosslinking agent composed of at least one polythiol (I) as defined above, which may be different from the polythiol or polythiols used for the preparation of the said product (P);

(c) in the event of crosslinking by the photochemical route, if appropriate a photoinitiator or a photoinitiating system, which can be used in combination with a photoactivating agent;

(d) in the event of crosslinking by the thermal route, an initiator which produces free radicals, which can be used in combination with an accelerator;

(e) if appropriate, at least one oligomer or monomer reactive diluent;

(f) if appropriate, at least one non-reactive diluent or solvent; and (g) if appropriate, at least one conventional additive, such as a pigment.

The photoinitiator or photoinitiating system is chosen in particular from those described above and is generally used in a proportion of 1 to 5% by weight with respect to the mass of the formulation of the product or products (P) with the polythiol or polythiols.

The thermal initiator and the accelerator used in combination are also chosen from those described above and are generally used in a proportion of 0.5 to 3% by weight and 0.1 to 1% by weight respectively with respect to the mass of the formulation of the product or products (P) with the polythiol or polythiols.

The compositions according to the invention can additionally comprise at least one from an oligomer or monomer reactive diluent, a non-reactive diluent or solvent and a conventional additive, such as a pigment.

Mention may be made, as oligomer or monomer reactive diluent, of vinyl monomers, such as vinyl acetate, styrene, vinyltoluene or divinylbenzene; acrylic and methacrylic esters, such as methyl (meth)acrylate, ethyl (meth)acrylate, isopropyl (meth)acrylate, n-butyl (meth)acrylate, isobutyl (meth)acrylate, 2-ethylhexyl (meth)acrylate, 2-hydroxyethyl (meth)acrylate, glycidyl (meth)acrylate, ethylene glycol di(meth)acrylate, diethylene glycol di(meth)acrylate, tetraethylene glycol di(meth)acrylate, glycerol di(meth)acrylate, glycerol tri(meth)acrylate, 1,3-propylene glycol di(meth)acrylate, dipropylene glycol di(meth)acrylate, tripropylene glycol di(meth)acrylate, 1,4-butanediol di(meth)acrylate, 1,2,4-butanetriol tri(meth)acrylate, 1,6-hexanediol di(meth)acrylate, 1,4-cyclohexanediol di(meth)acrylate, 1,4-benzenediol di(meth)acrylate, pentaerythritol tetra(meth)acrylate, 1,5-pentanediol di(meth)acrylate, trimethylolpropane di(meth)acrylate, trimethylolpropane tri (meth)acrylate, 2,2-dimethyl-3-hydroxypropyl 2,2-dimethyl-3-hydroxypropionate, isobornyl (meth)acrylate and tetrahydrofurfuryl (meth)acrylate; (meth)acrylates resulting from aromatic glycidyl ethers, such as bisphenol A diglycidyl ether, and from aliphatic glycidyl ethers, such as butanediol diglycidyl ether, specific examples of these comprising 1,4-butanediol diglycidyl ether di(meth)acrylate, bisphenol A diglycidyl ether di(meth)acrylate and neopentyl glycol diglycidyl ether di(meth)acrylate; and acrylamides or methacrylamides, such as (meth)acrylamide, diacetone (meth)acrylamide, N-(β-hydroxyethyl)(meth)acrylamide, N,N-bis(β-hydroxyethyl)(meth)acrylamide, methylenebis (meth)acrylamide, 1,6-hexamethylenebis(meth)acrylamide, diethylenetriaminetris(meth)acrylamide, bis (γ-(meth) acrylamidopropoxy)ethane and β-(meth)acrylamidoethyl acrylate.

Mention may be made, as non-reactive diluent or solvent, of ethyl acetate, butyl acetate, methoxypropanol, isopropanol, methyl ethyl ketone or acetone.

The pigments are in particular phthalocyanine blue and titanium dioxide.

The composition can also be placed in the form of an emulsion in water or of a dispersion in water.

If desired, the compositions of the present invention are stabilized. The formulation is stabilized with the help of one or more radical polymerization inhibitors employed in the conventional amounts chosen in particular from inhibitors of phenol type, quinones, phenothiazine and its derivatives, compounds carrying nitroxyl radicals, sterically hindered amines, aromatic nitro compounds, compounds comprising a nitroso or N-nitroso functional group, phosphites or thioethers. Mention may be made, as examples of inhibitors of phenol type, of, inter alia, hydroquinone, hydroquinone monomethyl ether, ortho-tert-butylphenol, 2,6-di-tert-butylphenol, 2,6-di-tert-butyl-para-nitrosophenol, para-cresol, 2,6-di-tert-butyl-para-cresol and 2,6-di-tert-butyl-para-methoxyphenol.

The present invention also relates to the products obtained by the crosslinking by the radical route of the composition as defined above, the said products being provided in the form of films, of films coating a substrate or of moulded items.

In order to obtain films, the composition is deposited as a thin layer on a substrate and is crosslinked by the radical route. The coating compositions according to the invention can be applied to the most diverse substrates: wood, paper, chipboard, particle board, metals, metals coated with a primer, glass, plastic or metallized plastic. The composition film can be applied to the substrate by immersion, spraying, coating with a roller or a curtain-coating device, and the like.

In order to obtain moulded items, the composition is introduced into a mould and is crosslinked by the radical route, the mould being a mould which is transparent to at least a portion of the radiation with wavelengths of between 180 and 400 nm in the case where the photochemical route is used.

When the compositions according to the invention are intended to be cured by ultraviolet light, use is made of any appropriate source which emits ultraviolet light having a wavelength of 180–400 nm, such as mercury arcs, carbon arcs, low pressure or medium pressure or high pressure mercury lamps, swirl-flow plasma arcs and ultraviolet lightemitting diodes. The power of these long-tube lamps is of the order of 80–240 watts per cm of tube length. Generally, the substrate coated with a thin film of the composition is moved along under one or more of the abovementioned lamps at a rate of between 1 and 300 meters per minute.

The following examples illustrate the present invention without, however, limiting the scope thereof. In these examples, the percentages are by weight, unless otherwise indicated.

SYNTHETIC EXAMPLE 1

12.6 g of 5-vinyl-2-norbornene (purity: 95%) are introduced into a reactor equipped with a condenser, a magnetic stirrer and a nitrogen feed which makes it possible to operate under an inert atmosphere. Heating is carried out to 70° C. and 8.5 g of bis(2-mercaptoethyl) sulphide are added in the space of 30 minutes using a dropping funnel.

During the addition, an exotherm is observed to occur and the temperature of the reaction mixture reaches 165° C. The reaction is monitored by infrared until complete disappearance of the —S—H band at 2571 $cm^{-1}$.

The product obtained exhibits a refractive index of 1.571 at 25° C.

SYNTHETIC EXAMPLE 2

The reaction is carried out in the same way as in Synthetic Example 1 using 11.2 g of 4-mercaptomethyl-3,6-dithia-1,8-octanedithiol (purity: 93%) and 15.2 g of 5-vinyl-2-norbornene.

The maximum temperature achieved during the addition of the thiol is 79° C. The product obtained exhibits a refractive index of 1.579 at 25° C.

SYNTHETIC EXAMPLE 3

The reaction is carried out in the same way as in Synthetic Example 1 using 12.2 g of pentaerythritol tetrakis(3-mercaptopropionate) and 12.6 g of 5-vinyl-2-norbornene.

The maximum temperature achieved during the addition of the thiol is 134° C. The product obtained exhibits a viscosity of 0.48 Pa·s at 25° C. and a refractive index of 1.531 at 25° C.

SYNTHETIC EXAMPLE 4

The reaction is carried out in the same way as in Synthetic Example 1 using 12.2 g of pentaerythritol tetrakis(3-mercaptopropionate) and 12 g of 5-ethylidene-2-norbornene (purity: 99%).

The maximum temperature achieved during the addition of the thiol is 95° C. The product obtained exhibits a viscosity of 7.66 Pa·s at 25° C. and a refractive index of 1.5445 at 25° C.

SYNTHETIC EXAMPLE 5

24 g of 5-ethylidene-2-norbornene are introduced into the equipment described in Synthetic Example 1 and are brought to 116° C. When the temperature is 116° C., the continuous addition of 24.4 g of pentaerythritol tetrakis (3-mercaptopropionate) over a period of time of 35 min (41.83 g/h) is begun. The temperature is maintained at 116° C. during the first 5 minutes of addition and then the temperature is decreased to 84° C. over a period of 30 minutes (temperature gradient of −1.07° C./min). When the addition is complete, the mixture is allowed to return to room temperature. The absence of the —S—H band at 2571 $cm^{-1}$ shows that all the dithiol has been consumed. The product obtained exhibits a refractive index of 1.5370 at 26° C. and a viscosity of 1.16 Pa·s at 25° C.

SYNTHETIC EXAMPLE 6

50.1 g of 5-vinyl-2-norbornene are introduced into the equipment described in Synthetic Example 1 and are brought to 118° C. When the temperature is 118° C., the continuous addition of 31.1 g of 2-mercaptoethyl sulphide over a period of time of 2 hours (15.55 g/h) is begun. The temperature is maintained at 118° C. during the first 10 minutes of addition and then the temperature is decreased to 82° C. over a period of one hour (temperature gradient of −0.6° C./min). A temperature of 82° C. is maintained until the end of the addition of the dithiol and then the mixture is allowed to return to room temperature. The absence of the —S—H band at 2571 $cm^{-1}$ shows that all the dithiol has been consumed. The product obtained exhibits a refractive index of 1.5610 at 24° C. and a viscosity of 0.06 Pa·s at 25° C.

SYNTHETIC EXAMPLE 7

The reaction is carried out in the same way as in Synthetic Example 6 using 50.9 g of 5-vinyl-2-norbornene and 37.5 g of 4-mercaptomethyl-3,6-dithia-1,8-octanedithiol (addition flow rate of 18.75 g/h). The product obtained exhibits a refractive index of 1.5725 at 23° C. and a viscosity of 0.2 Pa·s at 25° C.

SYNTHETIC EXAMPLE 8

The reaction is carried out in the same way as in Synthetic Example 6 using 38.9 g of 5-vinyl-2-norbornene and 37.5 g of pentaerythritol tetrakis(3-mercaptopropionate) (addition flow rate of 18.75 g/h). The product obtained exhibits a refractive index of 1.5275 at 26° C. and a viscosity of 0.27 Pa·s at 25° C.

In all the applicational examples which follow, unless otherwise indicated, the formulations are applied to glass using a K hand coater bar, so as to obtain a film with a thickness of 12 μm. When curing is carried out with ultraviolet light, the lamp used is an F450 (H-bulb) lamp with a power of 120 watts/cm sold by the company FUSION and the photoinitiators used are Darocure® 1173 (2-hydroxy-2-methyl-1-phenylpropan-1-one) and Irgacure® 184 (1-hydroxycyclohexyl phenyl ketone). The hardness is measured after 24 at room temperature.

Applicational Example 1

38.25 g of pentaerythritol tetrakis(3-mercaptopropionate) are added to 61.75 g of the product obtained in Synthetic Example 1. The refractive index of the formulation obtained is 1.564 at 25° C. A film exhibiting a 2 H pencil hardness is obtained after 2 passages under the lamp at the rate of 5 meters/min. When 1 g of Darocure® 1173 and 1 g of Irgacure® 184 are added, a dry film is obtained which exhibits a 4H pencil hardness after 2 passages under the lamp at 54 meters/min.

Applicational Example 2

The formulation described above comprising 1 g of Darocure® 1173 and 1 g of Irgacure® 184 is deposited in a watch glass (maximum thickness of 3 mm). After 5 passages under the lamp at the rate of 5 meters/min, a transparent and flexible crosslinked material is obtained.

Applicational Example 3

0.5 g of cobalt octoate and 1.5 g of methyl ethyl ketone peroxide are added to the formulation described in Applicational Example 2. The formulation is moulded in a watch glass. After 5 passages under the lamp at the rate of 5 meters/min and 30 min at 130° C., a flexible crosslinked material is obtained.

Applicational Example 4

22.95 g of pentaerythritol tetrakis(3-mercaptopropionate), 40 g of trimethylolpropane triacrylate (sold by the company Sartomer under the name SR 351), 1 g of Darocure® 1173 and 1 g of Irgacure® 184 are added to 37.05 g of the product obtained in Synthetic Example 1.

A dry film exhibiting a 2 H pencil hardness is obtained after 1 passage under the lamp at the rate of 54 meters/min.

Applicational Example 5

The formulation described above is cast in a watch glass. After 5 passages under the lamp at 5 meters/min, a transparent and hard crosslinked material is obtained.

Applicational Example 6

37.15 g of pentaerythritol tetrakis(3-mercaptopropionate), 1 g of Darocure® 1173 and 1 g of Irgacure® 184 are added to 62.85 g of the product obtained in Synthetic Example 2. The refractive index of the formulation is 1.565 at 25° C. A dry film exhibiting an H hardness is obtained after 3 passages at the rate of 54 meters/min.

Applicational Example 7

The formulation of Applicational Example 6 is cast in a watch glass. After 5 passages at the rate of 5 meters/min, an opaque and flexible crosslinked material is obtained.

Applicational Example 8

29.55 g of 4-mercaptomethyl-3,6-dithia-1,8-octanedithiol, 1 g of Darocure® 1173 and 1 g of Irgacure® 184 are added to 70.45 g of the product obtained in Synthetic Example 2. The formulation, which exhibits a refractive index of 1.594 at 25° C., is cast in a watch glass. After 5 passages at the rate of 5 meters/min, a transparent and flexible crosslinked material is obtained.

Applicational Example 9

13.9 g of 4-mercaptomethyl-3,6-dithia-1,8-octanedithiol, 19.6 g of pentaerythritol tetrakis(3-mercaptopropionate), 1 g of Darocure® 1173 and 1 g of Irgacure® 184 are added to 66.5 g of the product obtained in Synthetic Example 2. The refractive index of the formulation obtained is 1.579 at 25° C. A dry film exhibiting an H pencil hardness is obtained after 1 passage under the lamp at the rate of 54 meters/min.

Applicational Example 10

The formulation of Applicational Example 9 is cast in a watch glass. After 8 passages at the rate of 5 meters/min, a transparent and flexible crosslinked material is obtained.

Applicational Example 11

33.5 g of pentaerythritol tetrakis(3-mercaptopropionate) are added to 66.5 g of the product obtained in Synthetic Example 3. The refractive index of the formulation obtained is 1.531 at 25° C. A film exhibiting an H pencil hardness is obtained after 1 passage under the lamp at the rate of 54 meters/min.

Applicational Example 12

1 g of Darocure® 1173 and 1 g of Irgacure® 184 are added to the formulation of Applicational Example 11. The formulation is cast in a watch glass. After 5 passages under the lamp at the rate of 5 meters/min, a transparent and hard crosslinked material is obtained.

Applicational Example 13

26.35 g of 4-mercaptomethyl-3,6-dithia-1,8-octanedithiol, 1 g of Darocure® 1173 and 1 g of Irgacure® 184 are added to 73.65 g of the product obtained in Synthetic Example 3. The formulation, which exhibits a refractive index of 1.555 at 25° C., is cast in a watch glass. After 8 passages under the lamp at the rate of 5 meters/min, a transparent and flexible crosslinked material is obtained.

Applicational Example 14

33.5 g of pentaerythritol tetrakis(3-mercaptopropionate), 1.5 g of methyl ethyl ketone peroxide and 0.5 g of cobalt octanoate are added to 66.5 of the product obtained in Synthetic Example 3. The formulation is cast in a watch glass. After 1 hour at 60° C., a flexible crosslinked material is obtained.

Applicational Example 15

33.5 g of pentaerythritol tetrakis(3-mercaptopropionate) are added to 66.5 g of the product obtained in Synthetic Example 4. The refractive index of the formulation obtained is 1.5395 at 25° C. A film exhibiting an H hardness is obtained after 3 passages under the lamp at the rate of 54 meters/min.

Applicational Example 16

1 g of Darocure® 1173 and 4 g of Irgacure® 184 are added to the formulation of Applicational Example 15. The formulation is cast in a watch glass. After 5 passages under the lamp at the rate of 5 meters/min, a transparent and hard crosslinked material is obtained.

Test Examples 1 to 6
Mechanical Properties of Crosslinked Films

Crosslinked films with a thickness of 200 μm were prepared from the following formulation:

| | |
|---|---|
| Resin + crosslinking agent | 98% |
| Darocure 1173 | 1% |
| Irgacure 184 | 1% |
| | 100% |

Crosslinking is carried out by 3 passages at 5 m/min under the F450 (H-bulb) lamp with a power of 120 watts/cm.

$R^1$ is connected to the norbornene ring, it also being optional for the said ring to comprise other substituents chosen from $C_1$–$C_3$ alkyl groups, in proportions corresponding or substantially corresponding to one thiol group of the polythiol or polythiols (I) per mole of the compound or compounds (II), the thiol groups of the compound or compounds (I) adding predominantly to the cyclic double bond of the compound or compounds (II) and, on average, one ethylenic unsaturation of a compound (II) of the two which it carries remaining free; or sulphur product, (P'), obtained by the addition reaction of at least one polythiol (I) with at least one sulphur product (P), the double bonds of the said sulphur product (P) having been completely or substantially completely consumed, the sulphur product (P') obtained being a crosslinked product.

2. Sulphur product according to claim 1, characterized in that the compound or compounds of formula (II) is 5-vinylbicyclo[2.2.1]hept-2-ene and/or 5-ethylidene-bicyclo hept-2-ene.

3. Sulphur product according to claim 1, characterized in that the polythiols (I) are chosen from the compounds of formula $R^2SH_n$, in which:

$R^2$ is an n-valent aliphatic, aromatic or heterocyclic radical or an n-valent radical comprising a combination of these, it being optional for $R^2$ to comprise substituents, it being optional for the backbone or the

| Test example | RESIN according to Synthetic Example (amount) | CROSSLINKING AGENT* (amount) | $T\alpha^{(1)}$ (° C.) | tan δ max$^{(1)}$ | $E_r^{**(1)}$ (MPa) | HU$^{(2)}$ (MPa) | Tensile strength (MPa)$^{(3)}$ | Elongation$^{(3)}$ (%) | Modulus$^{(3)}$ (MPa) |
|---|---|---|---|---|---|---|---|---|---|
| 1 (Film 1) | 1 (394.4 g) | Trithiol (173.3 g) | 7 | 1.36 | 3.1 | 0.45 | 0.88 ± 0.7 | 42 ± 5 | 2.9 ± 0.1 |
| 2 (Film 2) | 1 (394.4 g) | Tetrathiol (244.35 g) | 19 | 1.04 | 5.8 | 0.81 | 1.8 ± 0.2 | 40 ± 5 | 5.8 ± 0.1 |
| 3 (Film 3) | 2 (620.6 g) | Trithiol (260 g) | 19 | 1.25 | 6.9 | 1 | 1.7 ± 0.3 | 28 ± 5 | 7.2 ± 0.1 |
| 4 (Film 4) | 3 (969.5 g) | Dithiol (308 g) | 6 | 1.46 | 4.9 | 0.7 | 1.5 ± 0.3 | 36 ± 6 | 5.3 ± 0.1 |
| 5 (Film 5) | 3 (969.5 g) | Trithiol (346.67 g) | 28 | 0.94 | 8.6–11 | 1.8 | 4 ± 0.4 | 53 ± 5 | 13 ± 0.3 |
| 6 (Film 6) | 3 (969.5 g) | Tetrathiol (488.7 g) | 31 | 1 | 11 | 7.8 | 10 ± 1 | 60 ± 11 | 255 ± 33 |

*Crosslinking agent:
Dithiol = Bis(2-mercaptoethyl) sulphide
Trithiol = 4-Mercaptomethyl-3,6-dithia-1,8-octanedithiol
Tetrathiol = Pentaerythritol tetrakis(3-mercaptopropionate)
**$E_r$ = rubbery plateau modulus
$^{(1)}$Measurements carried out on an RSAII from Rheometric Scientific at a frequency of 1 Hz
$^{(2)}$Measurement carried out on an H100 microdurometer from Fisher Instrumentation Electronique
$^{(3)}$Mean of 5 measurements carried out on an Instron device (5 m/min at 23° C.)

What is claimed is:

1. Sulphur product, (P), obtained by the addition reaction of at least one polythiol (I) with at least one compound of formula (II):

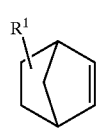

(II)

in which $R^1$ represents a linear or branched aliphatic residue comprising an ethylenic unsaturation double bond, it being optional for the latter to be that by which substituents to be interrupted by at least one heteroatom chosen from —O— or —S— and/or one group selected from the group consisting of

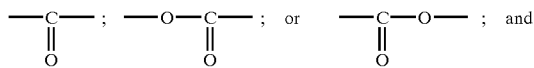

n is an integer from 2 to 6.

4. Sulphur product (P) according to claim 1, characterized in that the polythiols (I) are polythiols obtained by addition of a polythiol of formula $R^2SH_n$ to a compound of formula (II) with an excess of thiol, the sulphur product being uncrossinked.

5. Sulphur product according to claim 1, characterized in that the polythiol (I) is selected from the group consisting of dimercaptoethyl sulphide, 4-mercaptomethyl-3,6-dithia-1,8-octanedithiol, pentaerythritol tetrakis (3-mercaptopropionate) and pentaerythritol tetrakis(2-mercaptoacetate).

6. Process for the manufacture of the sulphur product as defined in claim 1, characterized in that a mixture of at least one polythiol (I) and at least one compound (II) is reacted at a temperature from 30 to 170° C., the proportions of the compounds (I) and (II) being chosen so that there is or that there is substantially one thiol group of the compound or compounds (I) per one mole of the compound or compounds (II), in order to obtain the crosslinkable product (P), and that, in order to obtain the product (P'), a mixture of the product (P) thus obtained and of at least one compound of formula (I) is reacted in stoichiometric proportions or substantially stoichiornetric proportions between the thiol groups and the double bonds.

7. Process according to claim 6, characterized in that the reaction of the compounds (I) and (II) is carried out in the presence of at least one catalyst chosen from free radical initiators selected from the group consisting of peroxides, peroxy esters, peroxydicarbonates, azo compounds, acids, Lewis acids, and amines.

8. Process according to claim 6, characterized in that the reaction of the compounds (I) and (II) is carried out in the absence of solvent.

9. Process according to claim 6, characterized in that the reaction of the compounds (I) and (II) is carried out in a solvent medium, the solvent being removed at the end of the reaction.

10. Process according to claim 6, characterized in that the reaction of the polythiol or polythiols (I) with the product (P) is carried out by exposure to radiation in the absence of photoinitiator or photoinitiating system, or alternatively in the presence of at least one photoinitiator or of a photoinitiating system.

11. Process according to claim 6, characterized in that the reaction of the polythiol or polythiols (I) with the product (P) is carried out thermally, in the presence of at least one initiator, a producer of free radicals, which can be used in combination with an accelerator.

12. Process according to claim 6, characterized in that a reaction mixture of the polythiol or polythiols (I) and of the reaction product (P) is deposited as a thin layer on a substrate and that the reaction is carried out by generation of free radicals in order to obtain the crosslinked product (P') in the form of a film.

13. Process according to claim 6, characterized in that the reaction mixture of the polythiol or polythiols (I) and of the reaction product (P) is introduced into a mould and that the reaction is carried out by generation of free radicals in order to obtain the crosslinked product (P') in the form of a moulded item, the mould being a mould which is transparent to at least a portion of the radiation with wavelengths of between 180 and 400 nm in the case where the free radicals arc generated by exposure to radiation.

14. Composition which can be crosslinked by generation of free radicals, wherein the radicals are generated thermally and/or by way of UV or visible irradiation or by way of an electron beam, characterized in that it comprises at least one crosslinkableproduct (P) as defined in claim 1.

15. Crosslinkable composition according to claim 14, characterized in that it comprises:

(a) at least one crosslinking product (P);

(b) at least one crosslinking agent composed of at least one polythiol (I);

(c) in the event of crosslinking by the photochemical route, if appropriate a photoinitiator or a photoinitiating system, which can be used in combination with a photoactivating agent;

(d) in the event of crosslinking by the thermal route, an initiator which produces free radicals, which can be used in combination with an accelerator;

(e) if appropriate, at least one oligomer or monomer reactive diluent;

(f) if appropriate, at least one non-reactive diluent or solvent; and (g) if appropriate, at least one conventional additive.

16. Films coating a substrate or moulded item obtained by the crosslinking by generation of free radicals of the composition as defined in claim 14.

17. Process for the manufacture of the film defined in claim 16, characterized in that the composition is deposited as a thin layer on a substrate and is crosslinked by generation of free radicals.

18. Process for the manufacture of molded articles characterized in that a composition as defined in claim 14 is introduced into a mould and that this composition is crosslinked by generation of free radicals, the mould being a mould which is transparent to at least a portion of the radiation with wavelengths of between 180 and 400 nm in the case where the free radicals are generated by exposure to radiation.

19. Composition which can be crosslinked by generation of free radicals, wherein the radicals are generated thermally and/or by way of UV or visible irradiation or by way of an electron beam, characterized in that it comprises at least one crosslinkable product (P) as defined in claim 2.

* * * * *